United States Patent [19]

Minoia et al.

[11] Patent Number: 5,811,451
[45] Date of Patent: Sep. 22, 1998

[54] PHARMACEUTICAL COMPOSITIONS COMPRISING AN OPIATE ANTAGONIST AND CALCIUM SALTS, THEIR USE FOR THE TREATMENT OF ENDORPHIN-MEDIATED PATHOLOGIES

[76] Inventors: Paolo Minoia, Via M. Viterbo 12, I-70013 Castellana Grotte, (Bari); Raffaele Luigi Sciorsci, Via Positano, 84/B, I-70014 Conversano, (Bari), both of Italy

[21] Appl. No.: 737,902

[22] PCT Filed: May 22, 1995

[86] PCT No.: PCT/EP95/01931

§ 371 Date: Nov. 21, 1996

§ 102(e) Date: Nov. 21, 1996

[87] PCT Pub. No.: WO95/31985

PCT Pub. Date: Nov. 30, 1995

[30] Foreign Application Priority Data

May 24, 1994 [IT] Italy .................................. MI94A1048

[51] Int. Cl.⁶ .................................................. A61K 31/485
[52] U.S. Cl. ........................... 514/443; 514/823; 514/816
[58] Field of Search ...................................... 514/816, 823, 514/443

[56] References Cited

U.S. PATENT DOCUMENTS 4,241,066 12/1980 Kobylecki et al. .

FOREIGN PATENT DOCUMENTS 876968 10/1979 Belgium .
0289070 11/1988 European Pat. Off. .
0506468 9/1992 European Pat. Off. .

OTHER PUBLICATIONS

J. of Biological Chemistry, vol. 264, No. 5, 1989, pp. 347–353, Attali et al.
Peptides, vol. 13, 1992, pp. 947–951, Wang et al.

*Primary Examiner*—Keith D. MacMillan
*Attorney, Agent, or Firm*—Bucknam and Archer

[57] ABSTRACT

The combined use of opiate antagonists and of calcium salts for the preparation of medicaments for the treatment of endorphin-mediated pathologies is described.

17 Claims, No Drawings

PHARMACEUTICAL COMPOSITIONS COMPRISING AN OPIATE ANTAGONIST AND CALCIUM SALTS, THEIR USE FOR THE TREATMENT OF ENDORPHIN-MEDIATED PATHOLOGIES

FIELD OF THE INVENTION

The present invention relates to the combined use of opiate antagonists and of calcium salts for the preparation of medicaments for the treatment of endorphin-related pathologies.

The invention also relates to pharmaceutical compositions for human and veterinary use containing as active principle opiate antagonists in combination with calcium salts and optionally with proteases, prostaglandins and Vitamin C and K. The compositions of the invention may optionally be in form of kit-of-parts, consisting of separate dosage forms for the contemporaneous or sequential administration of the above mentioned active principles.

BACKGROUND OF THE PRIOR ART

The neurons of the nigro-striatal system, together with many other nervous structures, synthesize low nuclear weight compounds, endorphins, having actions practically identical with that of phenantrene alkaloids of morphine. These endogenous opioids (endorphins) play an essential biological role in the Central Nervous System of every animal, man included.

The endogenous opiate peptides, enkephalins and endorphins, consisting of aminoacid (from 5 to 31) sequences, are present at the hypothalamic, cerebral and spinal level as well as in the endocrine glands (adrenal glands, hypophysis, ovaries, testis), and gastrointestinal system, muscle-skeletal system and immunitary system. The functions of the up-to-new known endorphins are multiple; the most known are: morphine-like analgesic properties, behavioural effects, neuromodulator functions.

These peptides, play also a remarkable role in functions such as memory, response to stress, pain transmission, regulation of appetite, temperature, respiratory frequency, libido, immunity etc.

The endorphins, ubiquitary present in mammals, inside and outside the central nervous system, derive from at least three different precursors: pre-pro-opiomelanocortine (POMC), pre-pro-enkephaline A and pre-pro-enkephaline B, yielding three classes of peptides related thereto, having well defined biological activity.

In particular, pre-pro-opiomelanocortine produces, as a result of lytic processes, differentiated in the various tissues, alpha-, beta- and gamma-endorphins; pre-pro-enkephalin A yields met-enkephalin and leu-enkephalin whereas pre-pro-enkephalin B is the precursor of alpha-neo-endorphin, beta-neo-endorphin and dinorphine. The role and distribution of these peptides in the various tissues have been widely studied, with particular reference to their ability of interacting with the opiate receptors.

The endorphins have been in fact recognized as defense agents able to induce analysis and sedation in organisms subjected to stress of different kind and aetiology.

For instance, an increased production of endorphins was noticed after traumatic injuries, nervous, endocrine, metabolic or infectious diseases, physical fatigue, delivery, insomnia, surgical operations, alimentary or pharmacological intoxication, etc.

The endorphins are found in the organisms both in a form bound to the receptors present in the various tissues and organs and in free form, in the plasma and in the liquor. The ratio between free and bound endorphins may be increased in relation to the increased production, the reduced catabolism or the competitive removal from the receptors of the bound endorphins, for instance by the opiate antagonists such as naloxone, naltrexone and derivatives and analogs.

The free endorphins, if not rapidly removed by catabolic mechanisms, bind again to the respective receptors, inducing a series of biochemical effects impairing the cellular metabolism, interfere with the nervous function and induce a pathogenetic action of the affected organs.

SUMMARY OF THE INVENTION

It has now been surprisingly found that the administration of opiate antagonists in combination with calcium ions is able to effectively antagonize said pathogenetic actions, resulting to be useful, both in human and in veterinary clinical practice, in pathologies characterized by high free and bound endorphin levels, hereinafter defined endorphin-related pathologies.

Without any connection to the validity of the invention, the proposed hypothesis is that the high tissue and circulating level of endorphins, both of physiological and pathological kind, interacts with the $Ca^{++}$ metabolism and with all the related or dependent functions. It is in fact presumed that, in the event of endorphins increase beyond the physiological limits, $Ca^{++}$ flow inside and outside the cells is somewhat impaired, resulting in endocellular and endotissutal calcium deficit with an increase of calcemia. Contemporaneously, it is probable that the signal of increased endocellular calcium request causes recruitment of external calcium towards the damaged tissues, where bound endorphins accumulate.

In other words, when different physiological or pathological conditions induce the endogenous increase of circulating endorphins, the latter bind to the opiate receptors in one or more structures or organs. While the presence of normal level of bound endorphins to the nervous receptors in any organ is physiological, on the contrary the increase of bound endorphins induces the accumulation of a large amount of these neuromodulators which, binding in large amounts to the receptors, form a sort of "endorphin cloud" involving alterations of the membrane potential and permeability in the nervous, muscular structures or in any cell having endorphin receptors. The alteration of the cell permeability mainly influences the activity and functionality of calcium channels and consequently all the related and consequent activities and functions.

Whenever high endorphin levels persist, the dysmetabolic processes start from the nervous terminations. In the acute processes, the block of the calcium entry and the mobilization of the intracellular calcium provide a metabolic accomodation which may become deadly, by removing the "endorphin cloud" and consequent sharp change of the membrane potential and entry into the bloodstream of calcium coming from within the cells previously blocked, in the absence of a suitable amount of calcium in the bloodstream.

It is presumed that the "endorphin cloud" first decreases the cellular and tissue functionality and reactivity, causing thereafter an abnormal activity through a kind of block of the $Ca^{++}$ channels present on the cell wall.

The outside and inside calcium block causes the affected cell to mobilize $Ca^{++}$ from the inner deposits in the endoplasmatic reticulum and in the mitochondria, so that its metabolic activity can be, at least partially, preserved. The contemporaneous extracellular calcium increase (increased calcemia) causes neuromuscular toxicity.

The calcium administration according to the invention prevents, in the case of hypocalcemia, the calcium outflow from cells, already impaired by $Ca^{++}$ deficit, into the bloodstream, with consequent worsening of the cellular damage and therefore of the pathology.

In any case, independently on the verification of the above reported mechanisms, previously never disclosed or hypothesized, the present invention allows to achieve surprising therapeutic results in endorphin-mediated pathologies.

The endorphin receptors, in addition to the Central Nervous System, are widespread in the organism, and therefore the pathologies which may be treated or alleviated by the present invention include diseases of the Central Nervous System such as paraplegia, nervous conducibility disturbances, Alzheimer's disease, cerebral ischemia, multiple sclerosis; gastro-intestinal diseases such as ulcers, irritable bowel syndrome; cardiovascular disease such as infarct, septic shock; dermatological diseases such as vitiligo, psoriasis, alopecia, dermatitis, traumatic injuries and burns; endocrinological and genito-urinary diseases such as LUF syndrome, ovaric micropolycystosis, impotence, hyperprolattinemia, hypophysary dwarfism, interstitial cystitis, primary amenhorrea.

The invention may also be advantageously used for the treatment of inflammatory conditions, infectious diseases, diseases of the muscle-skeletal system such as osteoporosis, arthritis, osteitis, periostitis, myopathies, autoimmune diseases.

It will be appreciated that the invention generally provides beneficial effects in those conditions where the natural tissue—or cell—repair processes should be preserved or re-established.

In veterinary medicine, in addition to the corresponding human pathologies cited above, the invention may be advantageously used for the treatment of specific conditions such as puerperal shock, in bovines, viral diseases in dogs and cats (parvovirus infections, distemper), MMA syndrome (metritis-mastitis-agalactia), Mulberry's heart disease, ruminal meteorism, Hoflund syndrome, osteo-articular traumas such as fractures, polyarthritis, osteomalacia, rachitism, hip dysplasia.

The invention may also be used for inducing and controlling the reproductive activity in mammals, fish and birds, for inducing the lysis of the corpus luteum, and to improve the athletic performance in horses and dogs; it is also useful for contraception.

The choice of the opiate antagonists will depend on several factors such as kinetics, potency, safety, pharmacological risks etc. For acute pathologies, for instance, the use of fast action and short half-life drugs such as naloxone is preferred whereas for chronic pathologies, long lasting drugs such as naltrexone will be preferably used.

Other opiate antagonists which may be used according to the invention comprise: dipremorphine, nalbuphine, betachloronaltrexonine, naltrexonazine, naloxazone, nalmefene, beta-funaltrexamine, ICI 174.864, 7-benzylidenenaltrexone (BNTX), naltrindole, norbinaltorphimine, norbinaltorphammine, naltribene (NTB), profadol, quadazocine, naloxonazine, D-Pen-Cys-Tyr-D-Trp-Orn-Thr-Pen-NH2 (CTOP), MR-2266, naltrindole-5'-isothiocyanate(5'-NTII), N-methyl-D-aspartate (NMDA), dextrorphane, methylnaltrexone (MNTX), DALCE(D-Ala2, Leu5, Cys6-enkephalin), methylnaloxonium, bremazocine and LY 274614.

It is anyhow possible to use any compound having opiate antagonist activity.

Also the posology and the administration route will depend on factors (animal species, weight, kind and seriousness of the pathology) which will be evaluated by the veterinary or by the physician. The dosage will generally be comprised from about ¹/₁₀ to about 10 times of that recommended for the widely known and classical indications of these drugs. For instance, in human medicine, naloxone may be initially administered at doses of 0.1–2 mg daily and naltrexone at doses of 5–50 mg daily, whereas doses of 10–20 mg of naltrexone are recommended for the manteinance therapy.

In veterinary, 5–50 mg of naloxone i.v. or i.m. may be administered to horses and bovine one or more times a day according to the pathology. In dogs, depending on the size, doses of 0.5–1 mg/kg are usually administered.

In the chronic pathologies in dogs it is preferable the administration of 5–10–20–50 mg of naltrexone per os, considering that the half-life of this drug is by far longer than that of naloxone, up to 2–3 days with the active metabolites. The pharmacological response depends on the used posology. In fact, minimal doses would induce only partial receptor activation whereas high doses have a complete and potent effect on the receptors. It is therefore possible to modulate the pharmacological treatment by regulating the binding of the opiate antagonist to different classes of receptor sites.

More precise indications on the dosages may be obtained from the quantitative determination of the endorphins bound to the affected tissues and organs, by means of a dynamic diagnostic method comprising a first radioimmunoassay and one or more subsequent assays after the administration of a specific endorphin antagonist, such as naloxone itself. The difference between the values of the free endorphins before and after the antagonist administration yields the value of bound endorphin and optionally, in the case of more assays after the antagonist administration, the binding kinetics of endorphins.

The parameters obtainable by said diagnostic method provide guidelines for therapeutic treatments according to the invention. The calcemia changes induced by the treatment of the invention may also provide useful hints for the therapy to be applied.

As calcium ion suppliers, all the soluble calcium salts compatible with the pharmaceutical use may be used, such as ascorbate, gluconate, glucoheptonate, dobesilate, glucobionate, levulinate, lactate, lactobionate, pantotenate, ketoglutarate, borogluconate, etc. Also the dosage of these compounds will be determined according to the already established therapeutic practice. See for instance Goodman & Gilman, "The pharmacological basis of therapeutics", VII ed., Macmillan Pub. Co., p. 1521.

The calcium salt may be administered both by oral and parenteral route, according to the specific therapeutic indication.

According to a preferred embodiment of the invention, the combination of an opiate antagonist and calcium may be added with proteases which, decomposing the free endorphins, increase the efficacy of the combination itself. Examples of suitable proteases, which may be administered at doses ranging form 40 to 160 U.P.F.U., include bromeline, papaine, chymotrypsine, trypsine, pepsine, subtilisine, proteinase A and K, kallicreine, elastase, chymopapaine, clostripaine, collagenase, metalloendo-peptidase, ficines.

The combination may also comprise other active principles, namely prostaglandins, phorbol, ATP, Vitamin C, levamisol, always at the dosage already known for these substances.

The preparation of the compositions of the invention, in combined or in "kit" form, is carried out using conventional excipients, such as those disclosed in "Remington's Pharmaceutical Sciences Handbook", Mack Pub. Co., NY, USA, XVII ed.

The following Examples further illustrate the invention.

EXAMPLE 1
Treatment of cows affected by milk fever

The hypocalcemic milk fever in cows provides an effective experimental model since the bovine species has a particularly complex calcium metabolism.

The milk secretion involves, in fact, the need to fix in the mammary glands, starting from the circulating liquids, about 1 g of calcium per kg of produced milk, whereas the total amount of calcium in the blood flow is 1.5 g. As a consequence, it is evident that, particularly at the beginning of lactation, the calcium turnover in cows should be particularly efficient and that in some cases there are block and interaction mechanisms, more serious in respect with what occurs in other species. This happens for instance during delivery when, as in every mammal, the maximum physiological increase of beta-endorphin and serious impairments of the $Ca^{++}$ metabolism occur.

30 Cows affected by milk fever were treated with 5 mg of naloxone, 50 g of calcium borogluconate i.v., trypsine 100 uFu and chymotrypsine 27.7 uFu i.m.

All the animals readily recovered and no fatal exitus occurred.

EXAMPLE 2
Treatment of cows affected by milk fever with meteorism

The milk fever in cows is sometimes combined by the contemporaneous block of the forestomachs motility and of the eructation reflex with consequent meteorism.

The administration of 5 mg of naloxone dissolved in a solution of 50 g of calcium gluconate in 500 ml of sterile water in one cow affected by the above mentioned complication with very marked tympanism induced a positive effect both on the milk fever and on the tympanism, after slow i.v. infusion of 250 ml of the calcium-naloxone, with recovery of the eructation reflex and expulsion of the excess gas in the rumen.

At the end of the infusion (500 ml), the cow stood up with remission of the symptoms. The administration of proteases (Endozym$^R$) finally induced the decrease of free endorphins concentrations.

EXAMPLE 3
Treatment of parvovirus-induced haemorrhagic gastroenteritis in dogs Parvovirus gastroenteritis in dogs is a virulent contagious disease which, if not treated, generally causes the animal's death. Even when a suitable therapy is applied, this disease has often an unfavourable prognosis. The disease is frequent in pups less than 1 year old. After incubation period of 3–4 days, the subject presents: anorexia, sensory depression, vomit, heamorrhagic diarrhoea, serious dehydratation, shock. The disease results in the subject's death in 2–5 days in 70% of the cases.

Recovery may occur in animals surviving after the fifth day only after complex therapies consisting in infusion of electrolytes, large amounts of vitamins C and K, antibiotics, cortisone, etc.

40 dogs affected by parvovirus gastroenteritis were treated i.v. daily with a sterile aqueous solution containing naloxone (0.5–1 mg), calcium gluconate (0.5 g), vitamin C (500–1000 mg), vitamin K (1 g).

The therapy induced the remission of symptoms already in the second day and the full restitution ad integrum in 3–5 days.

EXAMPLE 4
Treatment of parenchymatous mastitis by colibacilli in cows

The parenchymatous mastitis is a serious inflammation of a mammary section induced by colibacteria.

10 cows affected by this disease were treated with naloxone hydrochloride at the dose of 0.5 mg/100 kg body weight, calcium gluconate (50 g) and protease (Endozim$^R$). The antibiotic or sulfamidic specific for the pathology was contemporaneously administered. The treated subjects recovered their normal organic functions already at the first administration, with complete remission of the symptoms. The therapy lasted 2–3 days.

EXAMPLE 5
Treatment of distemper in the dog

8 Animals affected by distemper were treated with 0.5–1 mg of naloxone hydrochloride daily for one week, vitamin C (0.5–1 g/die of one week), calcium gluconate i.v. (0.5 g/die for one week), Endozym$^R$ and vitamin $B_1$ (500–1000 mg) parenterally for 1 week and antibiotics (cephalosporins+aminoglycosides i.m. for 1 week).

In each case, the forms were remarkably advanced, with manifest nervous symptoms.

The subjects improved after two-three days. The complete recovery even from nervous symptoms occurred after 5–15 days.

EXAMPLE 6
Effect of naloxone administration on healing process

The oral administration of naloxone to a clinically healthy 52 years old subject, appendicectomized 6 months before, affected by liponecrosis in the healing phase, induced a localized itching within 2–3 hours from the drug administration, at the laparotomy seat. In the following days, the healing process induced the formation of a small fistula from which some non-reabsorbed suture residues were eliminated. It is presumed that endorphins were responsible of the block of the healing process.

EXAMPLE 7
Treatment of the LUF syndrome

A particular form of anovulation, in human medicine, is known as luteinized unrupted follicle or LUF, characterized by regular menstrual flows and by a normal luteinization without ovulation. The LUF syndrome is considered to be responsible of unexplained sterility.

A woman affected by LUF syndrome, who was previously treated with gonadotropine since more than one year without ovulating had plasma concentration of beta-endorphin of 50 pg/ml, usually accepted as normal. The patient, after oral treatment with oral naloxone (25 mg), calcium (1 g), vitamin C (2 g) had a double ovulation after 4 days of therapy, conceived and a normal child was delivered at term.

EXAMPLE 8
Treatment of pathologies of the muscolo-skeletal system in the dog 1 Dog affected by hip dysplasia and two dogs with bone fractures of the limbs were treated. The animals, after pharmacological treatment according to the invention (0.2–0.5 mg of naloxone or 5–10 mg of naltrexone every 48 h for 2–4 weeks, 250–500 mg/die of calcium for 1 month, optionally proteases and vitamin C) readily improved (in 2–3 days) their pain and functional situation.

The bone callus rapidly formed in the fractured subjects and the consolidation times were about half of the usual ones.

EXAMPLE 9
Induction of apoptosis of corpus luteum in cyclc bovines 5 cyclic bovines in diestral phases were treated, for two consecutive days, with 5 mg of naloxone +2 g of Ca-borogluconate i.v. per 100 kg body weight.

The progressive damage of the corpus luteum was observed by ecography. All the treated bovines had estrus after 4–5 days from the end of the treatment. The level of circulating progesterone progressively approached zero. The results show that the endorphins mediate the calcium influx into the luteinic cells, influencing the apoptosis process of the corpus luteum.

EXAMPLE 10
Treatment of rachitic pups

12 Dogs affected by rachitism were treated i.m. with 0.1 mg/kg of naloxone and 50 mg/kg of calcium gluconate at alternate days for 1 month and Vitamin C (250 mg) for 1 month. All the animals finally recovered after 2 months from the beginning of the treatment. Pain disappeared already after the third day of treatment.

The results are particularly surprising since the administration of naloxone alone to rachitic pups induce in a few minutes acute hypocalcemia with tetanic crisis, whereas the administration of calcium salts alone induces vomit with marked tachycardia.

The treatment according to the invention is on the contrary free from side-effects and causes the full recovery of the treated subjects.

EXAMPLE 11
Therapy of the cholic syndrome in horses

11 Horses affected by cholic syndrome were treated i.v. with 0.6 g of calcium gluconate +1.2 mg of naloxone /100 kg body weight. The ready recovery of the good general conditions, pain disappearance and re-establishment of eminction and defecation occurred already after 15'–30' from the treatment.

EXAMPLE 12
Treatment of hypertropic osteodistrophy in the dog

A two months-old dog affected by hypertrophic osteodistrophy was treated i.m. with Calcium borogluconate (1 g) and naloxone (1 mg) die for 30 days. The dog showed a remarkable clinical and functional recovery, confirmed by radiological examination showing the normalization of periosteum and disappearance of the Winberger sign.

We claim:

1. The method of treatment of a living subject suffering from an endorphin-mediated pathology which consists of administering to said living subject a composition comprising an opiate antagonist (a) and a bioavailable calcium salt (b).

2. The method according to claim 1 wherein said opiate antagonist is a member selected from the group consisting of naloxone, naltrexone, dipremorphine, nalbuphine, betachloro-naltrexonine, naltrexonazine, naloxazone, nalmefene, beta-funaltrexamine, ICI 174.864, 7-benzylidenenaltrexone (BNTX), naltrindole, norbinaltorphimine, norbinaltorphammine, naltribene (NTB), profadol, quadazocine, naloxonazine, D-Pen-Cys-Tyr-D-Trp-Orn-Thr-Pen-NH2 (CTOP), MR-2266, naltrindole-5'-isothiocyanate(5'-NTII), N-methyl-D-aspartate (NMDA), dextrorphane, methylnaltrexone (MNTX), DALCE(D-Ala2, Leu5, Cys6-enkephalin), methylnaloxonium, bremazocine and LY 27614.

3. The method according to claim 1 wherein said composition additionally contains at least one member selected from the group consisting of proteases, prostaglandins, phorbol, Vitamin C and Vitamin K.

4. The method according to claim 3 wherein said composition contains a protease and the protease is a member selected from the group consisting of bromeline, papaine, chymotrypsine, trypsine, pepsine, subtilisine, proteinase A and K, kallicreine, elastase, chymopapaine, clostripaine, collagenase, metalloendopeptidase and ficines.

5. The method according to claim 1 wherein said administration is carried out intravenously, parenterally or orally.

6. The method according to claim 1 wherein said pathology is rachitism, said bioavailable calcium salt is calcium gluconate and said opiate antagonist is naloxone.

7. The method according to claim 1 wherein said pathology is an inflammatory condition, an infectious disease, osteoporosis and an autoimmune disease.

8. The method according to claim 1 wherein said calcium salt is a soluble calcium salt compatible with the pharmaceutical use and is a member selected from the group consisting of calcium ascorbate, gluconate, glucoheptonate, dobesilate, glucobionate, levulinate, lactate, lactobionate, pantotenate, ketoglutarate, and borogluconate.

9. The method according to claim 1 wherein said living subject is a cow affected by milk fever, said opiate antagonist is naloxone and said calcium salt is calcium borogluconate.

10. The method according to claim 1 wherein said living subject is a cow affected by milk fever meteorism and said opiate antagonist is naloxone and said calcium salt is calcium gluconate.

11. The method according to claim 1 wherein said living subject is a dog affected by parvovirus gastroenteritis, said opiate antagonist is naloxone and said calcium salt is calcium gluconate.

12. The method according to claim 1 wherein said living subject is a cow affected by parenchymatous mastitis, said opiate antagonist is naloxone hydrochloride, said calcium salt is calcium gluconate.

13. The method according to claim 1, said living subject is a dog affected by distemper, said opiate antagonist is naloxone hydrochloride and said calcium salt is calcium gluconate.

14. The method according to claim 3 wherein said living subject is a woman affected by luteinized unrupted follicle, said opiate antagonist is naloxone, and said composition contains Vitamin C.

15. The method according to claim 1 wherein the living subject is a cow suffering from damage of the corpus luteum, said opiate antagonist is naloxone and said calcium salt is calcium borogluconate.

16. The method according to claim 1 wherein said living subject is a horse affected by cholic syndrome, said calcium salt is calcium gluconate and said opiate antagonist is naloxone.

17. The method according to claim 1 wherein said living subject is a dog affected by hypertrophic osteodistrophy, said calcium salt is calcium borogluconate and said opiate antagonist is naloxone.

* * * * *